(12) United States Patent
Harrold

(10) Patent No.: US 8,521,244 B2
(45) Date of Patent: Aug. 27, 2013

(54) PHYSIOLOGICAL PARAMETER MONITORING APPARATUS

(75) Inventor: Lewis Norman Harrold, Georgetown, MA (US)

(73) Assignee: Analogic Corporation, Peabody, MA (US)

( * ) Notice: Subject to any disclaimer, the term of this patent is extended or adjusted under 35 U.S.C. 154(b) by 1015 days.

(21) Appl. No.: 12/560,744

(22) Filed: Sep. 16, 2009

(65) Prior Publication Data
US 2011/0066013 A1     Mar. 17, 2011

(51) Int. Cl.
*A61B 5/1455* (2006.01)
(52) U.S. Cl.
USPC .......................... 600/323; 600/344
(58) Field of Classification Search
USPC ................. 600/310, 322, 323, 340, 344, 473, 600/476
See application file for complete search history.

(56) References Cited

U.S. PATENT DOCUMENTS

| | | | |
|---|---|---|---|
| 5,584,296 A | 12/1996 | Cui et al. | |
| 6,262,798 B1 | 7/2001 | Shepherd et al. | |
| 6,304,767 B1 | 10/2001 | Soller et al. | |
| 6,564,088 B1 | 5/2003 | Soller et al. | |
| 6,577,884 B1 * | 6/2003 | Boas ............................ | 600/310 |
| 6,792,300 B1 | 9/2004 | Diab et al. | |
| 7,062,306 B2 | 6/2006 | Benaron et al. | |
| 7,120,482 B2 * | 10/2006 | Kimura ......................... | 600/344 |
| 7,139,600 B2 * | 11/2006 | Maki et al. ..................... | 600/344 |
| 7,343,186 B2 | 3/2008 | Lamego et al. | |
| 7,376,454 B2 | 5/2008 | Casciani et al. | |
| 2002/0151774 A1 | 10/2002 | Soller et al. | |
| 2005/0259254 A1 | 11/2005 | Soller et al. | |
| 2007/0038041 A1 | 2/2007 | Yang et al. | |
| 2008/0017800 A1 | 1/2008 | Benni | |
| 2008/0132771 A1 | 6/2008 | Parker et al. | |

OTHER PUBLICATIONS

Lima et al., Noninvasive monitoring of peripheral perfusion, Intensive Care Med., Sep. 2005, pp. 1316-1326, abstract attached.

* cited by examiner

*Primary Examiner* — Eric Winakur
(74) *Attorney, Agent, or Firm* — Driggs, Hogg, Daugherty & Del Zoppo, Co. LPA

(57) ABSTRACT

A tissue oximeter sensor includes a substrate with a non-zero finite depth and first and second major sides. At least a first material free region extends along the depth from one of the sides to the other of the two sides forming a first well in the substrate. One of the sides of the substrate is configured to be removeably affixed to a human or animal subject. The sensor also includes a first channel with first and second end portions. One of the end portions of the first channel is selectively positioned in the first well along the depth alternatively at one of a plurality of different depth positions. The first channel routes radiation at least one of from the first end portion to the second end portion or from the second end portion to the first end portion.

26 Claims, 5 Drawing Sheets

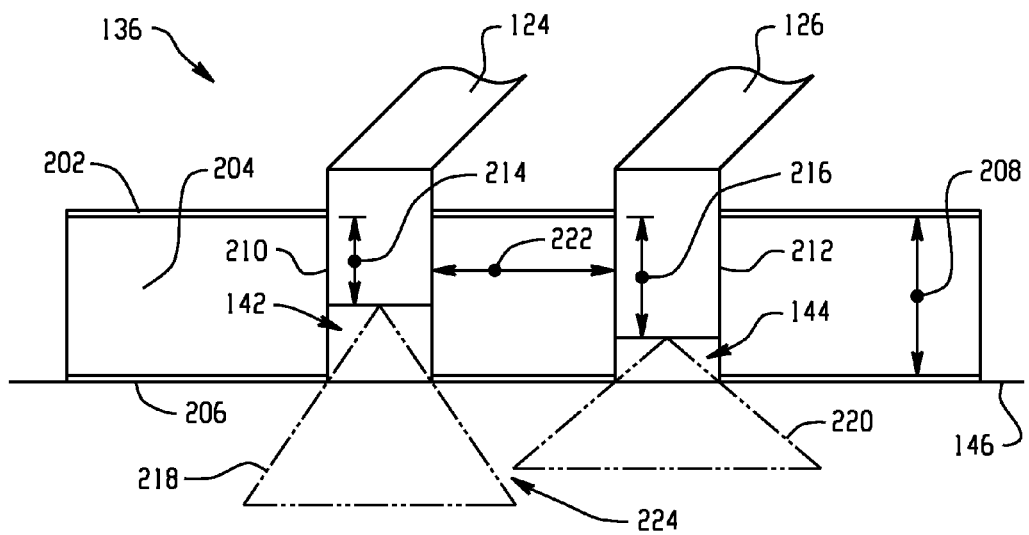
Fig. 2
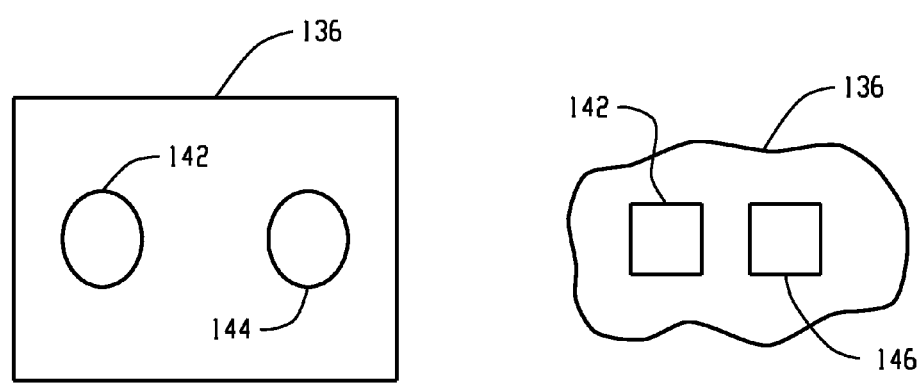
Fig. 3
Fig. 4

PHYSIOLOGICAL PARAMETER MONITORING APPARATUS

TECHNICAL FIELD

The following generally relates to a physiological parameter monitoring apparatus and is described with particular application to a physiological parameter monitoring apparatus that is configured to monitor tissue oxygenation.

BACKGROUND

An oximeter senses signals that can be used to determine blood oxygenation, or oxygen saturation of blood of a patient. One oximeter has included an emitter and sensor. The emitter emits electromagnetic radiation (commonly referred to as light) in the visible and the near infrared regions of the electromagnetic spectrum, and the sensor senses red and/or infrared light and generates signals indicative of the sensed light.

With a transmission-based oximeter, the emitter and the sensor are located opposite each other across an examination region, and the emitter emits light that traverses vascular or interstitial tissue of anatomy (e.g., a finger, an earlobe, etc.) located in the examination region and is sensed by the sensor. With a reflectance-based oximeter, the emitter and the sensor are located on the same side of the examination region, and the sensor senses light emitted by the emitter that reflects from the vascular tissue.

The sensed signals are used as inputs to algorithms, which are used to determine oxygen absorbance values. Generally, at known selected wavelengths of light, oxygenated hemoglobin absorbs more infrared light than red light, and deoxygenated hemoglobin absorbs more red light than infrared light. Algorithms compute a ratio of the absorbance of red light to the absorbance of infrared light and that is then used as an estimate of the percentage of the hemoglobin that is bound with oxygen, which is used to estimate the oxygen saturation of the blood.

Another device uses near infrared spectroscopy (NIRS) to determine tissue oxygenation in interstitial fluids within the examination region.

The above-noted devices have employed a compact light emitting diode (LED) integrated chip (IC) mounted on a sensor assembly or rigid light bundles mounted to the assembly. Unfortunately, the sensor assembly can be relatively costly, and the rigid light bundles can be cumbersome. In addition, the above-noted devices use custom algorithms, whose computations depend on the precise absorbance at a number of light wavelengths, and precise angles of detection, all of which dictate the precise location of the LED IC on the assembly.

SUMMARY

Aspects of the application address the above matters, and others.

In one aspect, a tissue oximeter sensor includes a substrate with a non-zero finite depth and first and second major sides. At least a first material free region extends along the depth from one of the sides to the other of the two sides forming a first well in the substrate. One of the sides of the substrate is configured to be removeably affixed to a human or animal subject. The sensor also includes a first channel with first and second end portions. One of the end portions of the first channel is selectively positioned in the first well along the depth alternatively at one of a plurality of different depth positions. The first channel routes radiation at least one of from the first end portion to the second end portion or from the second end portion to the first end portion.

In another aspect, a method includes selectively installing a first end region of a set of flexible fiber optic fibers in a well of a tissue oximeter sensor substrate to one of a plurality of different depth positions in the well, wherein the installed position corresponds to a tissue oximeter processing algorithm of a given tissue oximeter processing unit.

In another aspect, a physiological parameter monitoring apparatus includes a processing unit, including an optical source and an optical detector, flexible optical transmit and receive channels having first and second end regions, and a flexible substrate that carries the first end regions of the flexible optical transmit and receive channels. The first end regions are installed at predetermined depths of the flexible substrate. The installed depths correspond to a tissue oximeter processing algorithm of the processing unit. The flexible optical transmit channel routes optical radiation emitted by a source from the second end region of the flexible optical transmit channel to a target adjacent the first end region. The flexible optical receive channel routes optical radiation traversing or reflecting from the target to the detector.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 2 illustrates a cross-sectional view of an example sensor substrate with channels installed therein;

FIG. 3 illustrate an example alternative substrate shape;

FIG. 4 illustrate another example alternative substrate shape;

DETAILED DESCRIPTION

Figure 1:
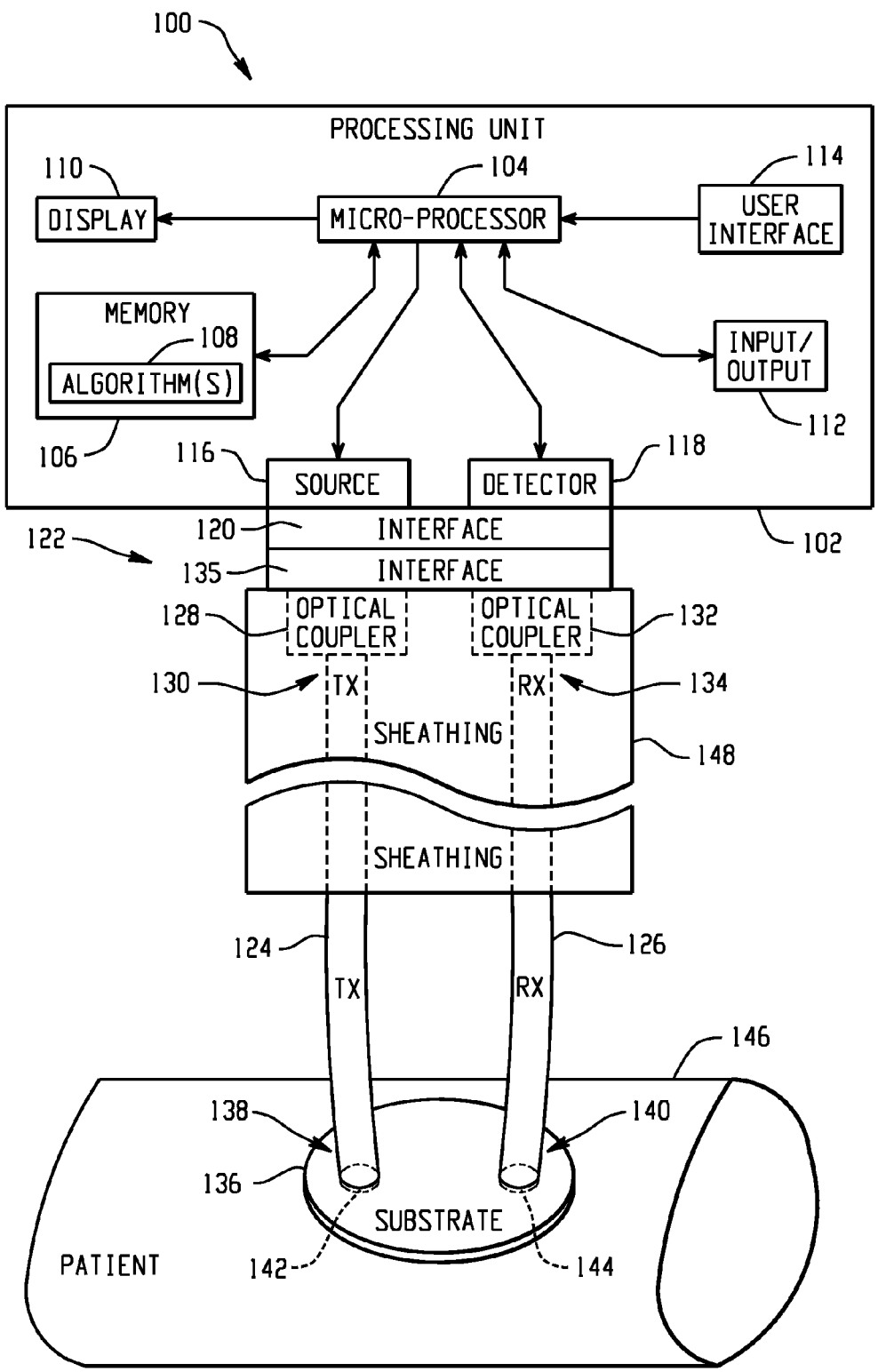
FIG. 1 illustrates an example apparatus.

FIG. 1 illustrates an example physiological parameter monitoring apparatus 100 that at least determines physiological information about a human or animal subject based on the affect that a presence (or concentration) of a substance (such as oxygenated hemoglobin, glucose, lipids, or other dissolved chemical) in tissue has on the optical properties of the tissue. For sake of brevity and clarity, the apparatus 100 is described in connection with determining tissue oxygenation (and/or tissue deoxygenation).

The physiological parameter monitoring apparatus 100 includes a tissue oximetry monitor or processing unit 102 with a microprocessor 104 and memory 106. The microprocessor 104 is configured to execute computer executable instructions in the memory 106, including one or more instructions corresponding to a processing algorithm 108 in the memory 106. In one embodiment, the processing algorithm 108 includes one or more instructions for determining a concentration of oxygenated and/or deoxygenated hemoglobin in blood from a sensed physiological parameter. The microprocessor 104 also controls one or more of the other elements of the processing unit 102.

A display 110 displays information, including information indicative of the determined concentration of the oxygenated and/or the deoxygenated hemoglobin in the blood. Examples of a suitable display include, but are not limited to, a liquid crystal display (LCD), a seven-segment display, and/or other display. One or more audible indicators may additionally or alternatively be included in the processing unit 102 and provide a warning, a message, an audible presentation of the determined concentration, and/or other information. One or more tactile (e.g., vibration) indicators may also additionally or alternatively be included for presenting information.

Input/output (I/O) 112 provides at least one channel or port for conveying information to the processing unit 102 and/or from the processing unit 102. For example, in one instance the processing algorithm 108 is conveyed to the processing unit 102 via the I/O 112. In another example, the sensed information and/or the determined concentration is conveyed from the processing unit 102 to another device via the I/O 112. Such data can be conveyed to a central monitoring station, a computer, a printer, etc. through a direct connection and/or over a network. The I/O 112 may include Universal Serial Bus (USB), radio frequency (RF), infrared (IR), and/or other communication paths.

A user interface 114 includes one or more controls that allow a user to provide input for controlling the processing unit 102. For example, the user interface 114 may include a control for turning the apparatus 100 on and off, a control for activating the processing unit 102 to emit and/or detect radiation, a control for initiating transferring data to and from the processing unit 102, a control for determining the displayed information, and/or a control for otherwise controlling the apparatus 100. The illustrated user interface 114 is part of the processing unit 102. However, in another embodiment the user interface 114 is part of a device remote from the processing unit 102 such as a remote control, a central monitoring station, and/or other device.

The processing unit 102 further includes an electromagnetic radiation source 116. The illustrated radiation source 116 emits optical electromagnetic radiation ("light"). In one non-limiting embodiment, the radiation source 116 is configured to emit broadband optical radiation in the visible and/or near infrared regions of the electromagnetic spectrum, for example, with a wavelength between four hundred (400) and two thousand five hundred (2500) nanometers (nm) ("light"). In other embodiments, the radiation source 116 is configured to emit radiation in other wavelength ranges. Non-limiting examples of a suitable radiation source 116 includes, but is not limited to, a light emitting diode (LED) such as a white light LED, a laser, an incandescent bulb, a fluorescent lamp, an arc lamp, and/or other optical source.

The processing unit 102 also includes a radiation sensitive detector 118. The detector 118 detects electromagnetic radiation, including radiation emitted by the radiation source 116, and generates a signal indicative thereof. In one non-limiting embodiment, the radiation sensitive detector 118 is configured to detect broadband optical radiation in the visible and/or near infrared regions of the electromagnetic spectrum. In other embodiments, the radiation sensitive detector 118 is configured to detect other radiation in other ranges. Examples of a suitable detector includes a photosensor such as, but not limited to, a photodiode, a photomultiplier, a charge-coupled device (CCD), and/or other photosensor or optical conversion device.

A communications interface 120 provides an interface for conveying radiation emitted by the source 116 and receiving radiation to be detected by the detector 118.

A sensing portion 122 includes transmit (TX) and receive (RX) pipes or channels 124 and 126. The illustrated channels 124 and 126 are flexible (non-rigid) optical channels, and each of the channels 124 and 126 includes one or more bundles of flexible fiber-optic fibers. An example of a suitable flexible plastic fiber optic fiber bundle includes, but is not limited to, a GORE™ Fiber Optic Ribbon Cable, which is manufactured by W. L. Gore & Associates of Newark, Germany.

A first optical coupler 128 is coupled to a first end region 130 of the transmit channel 124, and a second optical coupler 132 is optically coupled to a first end region 134 of the receive channel 126. The first optical coupler 128 directs radiation to one or more of the fiber optic fibers of the transmit channel 124, and the second optical coupler 132 directs radiation received from one or more of the fiber optic fibers. An example of a suitable optical coupler includes an optical taper or the like. An example of a suitable optical taper includes, but is not limited to, a SCHOTT Fused Fiber Optic Taper, which is manufactured by SCHOTT of Elmsford, N.Y., USA. The first and second optical couplers 128 and 132 may improve optical efficiency relative to a configuration in which the optical couplers 128 an 132 are omitted from the apparatus 100.

A communications interface 135 provides an interface for coupling the channels 124 and 126, via the optical couplers 128 and 132, to another device such as the processing unit 102. In the latter instance, the communication interfaces 135 and 120 are complementary communication interfaces, and couple the optical couplers 128 and 132 respectively with the source 116 and the detector 118 of the processing unit 102. When the communications interfaces and 120 and 135 are coupled, the transmit channel 124 routes radiation from the source 116, and the receive channel 126 routes radiation to the detector 118.

A substrate 136 carries second end regions 138 and 140 of the transmit channel 124 and the receive channel 126. In the illustrated embodiment, material free regions or wells 142 and 144 of the substrate 136 carry the second end regions 138 and 140, and the wells 142 and 144 are arranged with respect to each other so that the receive channel 126 receives radiation emitted by the source 116 that is reflected by structure in the emission path. The illustrated substrate 136 is configured as a wearable patch. The substrate 136 is configured to be removeably affixed to the anatomical structure 146 such as an arm, a leg, a finger, a foot, and/or other anatomical structure adjacent to tissue of interest such as vascular tissue or other tissue. Such a patch may be disposable. In this instance, the patch can be discarded upon removal from the anatomical structure 146. In another instance, the patch is cleanable and reusable. In this instance, the patch can be cleaned and/or sterilized after use and reused with the same patient or a different patient.

As described in greater detail below, the channels 124 and 126 and the substrate 136 include a flexible material, and the spacing between the wells 142 and 144 and location of the channels 124 and 126 along a depth of the wells may be based on various criteria such as, but not limited to, the input of a particular tissue oximetry processing algorithm 108 in the memory 106, a electromagnetic radiation wavelength range of interest, an electromagnetic emission radiation efficiency, radiation source power consumption, an electromagnetic radiation detection efficiency, and/or other criteria. In one embodiment, such a sensing portion 122 may provide a compact, power efficient, relatively low cost, flexible, and/or mass producible light piping device for a plurality of different tissue oximeters with similar or different tissue oximetry processing algorithms, emission and/or detection efficiencies, wavelengths of interest, and/or source power consumption ranges.

A sheathing 148 surrounds at least a sub-portion of the channels 124 and 126. In one instance, the sheathing 148 shields the channels 124 and 126 from the surrounding environment. As such, the sheathing 148 may protect the channels 124 and 126 and hence the fiber optic fibers therein from debris, foreign matter, human touch, and/or other sources that may damage the fibers or adversely affect the radiation being routed through the channels 124 and 126.

Note that the relative sizes of the various illustrated elements of the apparatus 100 are for explanatory purposes and not limiting.

FIG. 2 illustrates a cross sectional view of an example of the substrate 136 with the channels 124 and 126 installed in the wells 142 and 144. The illustrated layer 204 is formed from a flexible material, such as polyester, a polyimide film or other material. Layers 202, 206 may be of common, flexible, low cost materials like polyethylene, polypropylene, or other material. The illustrated substrate 136 includes first and second major sides and a plurality of layers, including a top layer 202, an intermediate layer 204, and bottom layer 206.

The top layer 202 may protect the substrate and the channels 124 and 126 installed therein from the surrounding environment. In another embodiment, the top layer 202 and the intermediate layer 204 are part of the same layer. The bottom layer 206 includes an adhesive such as an epoxy, tape, and/or other adhesive that facilitates removeably affixing the flexible substrate 136 to the anatomical structure 146. The adhesive may be a biocompatible-adhesive or other adhesive suited for removably adhering to human or animal skin. When affixed to a patient, the flexible substrate 136 flexes to conform to the contour of the anatomical structure 146 to which the substrate 136 is affixed.

The intermediate layer 204 has a finite depth 208 and material free regions 210 and 212 that extend through the depth 208 and define the wells 142 and 144. The wells 142 and 144 are spaced apart from each other by a distance 222. In the illustrated embodiment, the transmit channel 124 is installed in the well 142 along a first sub-portion 214 of the depth 208, and the radiation emanating from the channel 124 defines an emission zone 218. The receive channel 126 is installed in the well 144 along a second sub-portion 216 of the depth 208, and the radiation from a detection zone 220 enters the channel 126. Walls of the wells 142 and 144 may facilitate shielding the anatomical structure 146 and/or the detector 118 from radiation not emitted by the source 116.

The depths 214 and 216 at which the channels 124 and 126 are located in the wells 142 and 144 may, at least in part, facilitate defining the emission and the detection zones 218 and 220 and zone spacing 224 therebetween. Note that each of the channels 124 and 126 can be affixed in the wells 142 and 144 at one of a plurality of different locations along the depth 208. The extent to which the wells 142 and 144 and thus the channels 124 and 126 are spaced apart (spacing 222) also, at least in part, facilitates determining the spacing 224 between the emission and detection zones 218 and 220. In the illustrated embodiment, the spacing 224 is such that the emission and the detection zones 218 and 220 do not overlap. In other embodiments, the emission and the detection zones 218 and 220 partially or fully overlap.

For a given emission wavelength of the processing unit 102, the location of the channel 124 in the well 142 also facilitates determining a penetration depth of the emitted radiation in the anatomical structure 146. Further, the location of the channel 124 in the well 142 may also affect emission radiation efficiency within the zones 218, 220 as radiation striking the wall of the well 142 may be absorbed and/or otherwise attenuated and not illuminate the anatomical structure 146 which contains the zones 218 and 220. Similarly, the location of the channel 126 in the well 144 may affect radiation efficiency detection as reflected radiation striking the wall of the well 144 may be absorbed and/or otherwise attenuated and not be received by the detector 118. The location of the wells 142 and 144 and the channels 124 and 126 may also facilitate optimizing power efficiency, for example, through the alignment of the zones 218 and 220.

In one non-limiting embodiment, the particular depths 214 and 216 and spacing 222 for a substrate 136 correspond to one or more of the processing algorithm 108, an emission and/or detection wavelength range of interest, an emission radiation efficiency, a radiation detection efficiency, a predetermined source power consumption, and/or other criteria. Note that for a given amount of radiation penetrating the anatomical structure 146, source power consumption can be decreased with increased emission radiation efficiency. Alternatively, for a given source power consumption, the amount of radiation penetrating the anatomical structure 146 can be increased with increased emission radiation efficiency.

As such, different sensing portions 122 may be configured to correspond to different processing units 102. In addition, multiple different sensing portions 122 may be used with a single processing unit 102 that includes suitable processing algorithms corresponding to the multiple different sensing portions 122. A single sensing portion 122 may also be used interchangeably with multiple of the same or different processing units 102.

The channels 124 and 126 are secured in the wells 142 and 144 the depth 208 via an adhesive such as an epoxy, a glue, a tape, and/or other adhesive. In the illustrated embodiment, the flexible channels 124 and 126 extend out of the wells 142 and 144 and then bend through an angle of about ninety-degrees and extend along a surface of the top layer 202 of the substrate 136. In other embodiments, the flexible channels 124 and 126 can be otherwise configured, for example, to bend through another angle such as an angle between zero and ninety-degrees with respect to the substrate 136. The particular angle may depend on the substrate shape, the light wavelengths, and the anatomy to which the substrate 136 is affixed, etc.

Variations are contemplated.

In FIGS. 1 and 2, the substrate 136 and wells 142 and 144 are elliptically shaped. In FIG. 3, the substrate 136 is rectangular in shape with circular shaped wells 142 and 144, and in FIG. 4 the substrate 136 is irregular in shape with square shaped wells 142 and 144. Still other shapes are contemplated herein. For example, in one instance, the shape of the substrate 136 may coincide with particular anatomic structure, such as a breast or finger. As such, substrate configured to be placed around a finger may be shaped based on a typical shape of a finger, whereas a substrate configured to be placed on the forehead may be accordingly shaped based the typical shape of a forehead.

Figure 5:
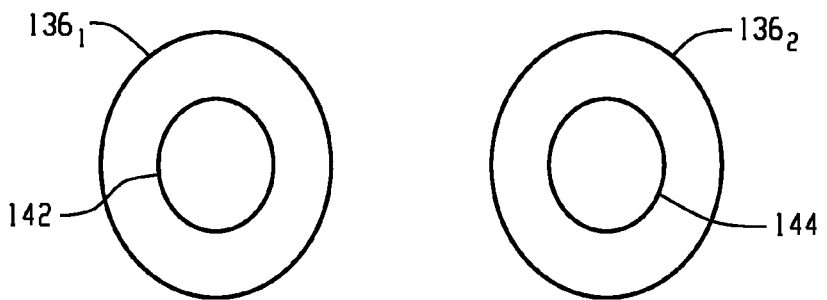
FIG. 5 illustrates an example in which the substrate includes two physically separate substrates.

FIG. 5 shows an embodiment in which the wells 142 and 144 are located on separate individual substrates $136_1$ and $136_2$.

In another embodiment, the channels 124 and 126 share a single common well (e.g., the well in substrate 136₁ or 136₂).

Note that the above-illustrated embodiment includes two channels (channels 124 and 126). In another embodiment, there may be a single channel or more than two channels.

Figure 6:
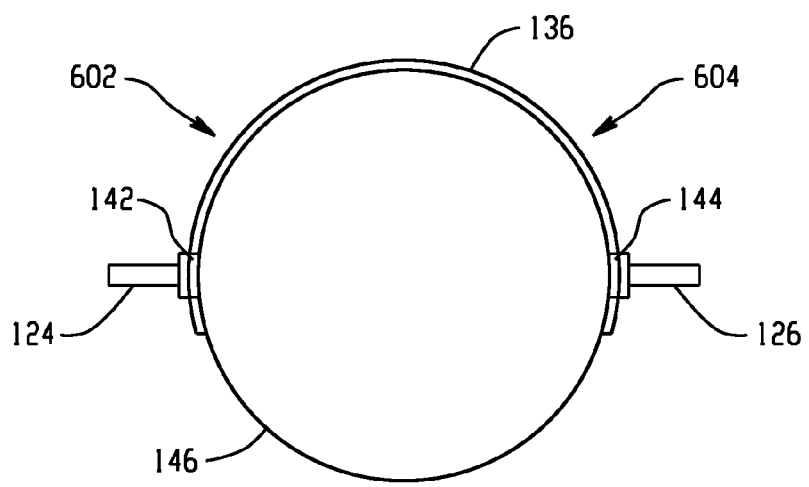
FIG. 6 illustrates an example substrate configured for transmission based oximetry.

FIG. 6 illustrates an embodiment in which the substrate 136 is configured for use with a transmission based tissue oximetry processing algorithm. In this embodiment, the wells 142 and 144 are located so as to be positioned on opposites sides 602 and 604 of the anatomical structure 146, and the receive channel 126 receives transmission radiation (emitted by the source 116) that traverses the anatomical structure 146.

Figure 7:
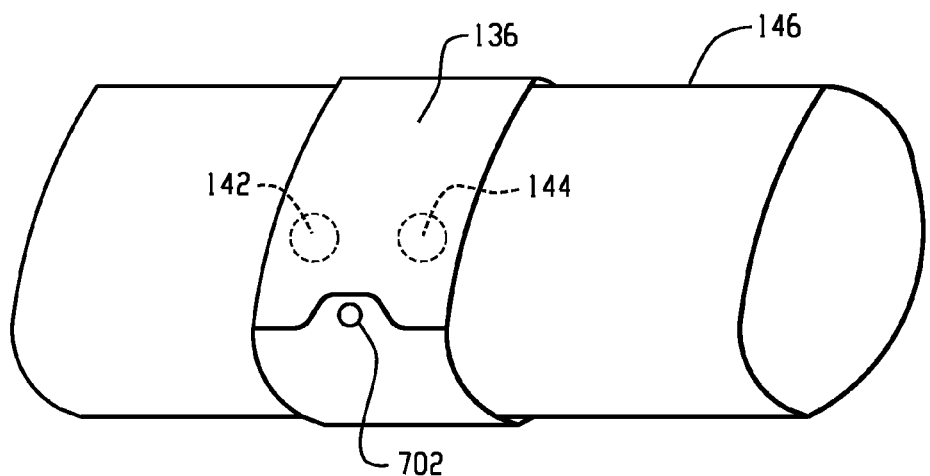
FIG. 7 illustrates an example substrate configured to wrap around an anatomical structure.

FIG. 7 illustrates an embodiment in which the substrate 136 is configured to be wrapped around the anatomical structure 146. In the illustrated embodiment, the adhesive layer 206 is omitted from the substrate 136, and the substrate 136 includes a fastener 702 that facilitates affixing the substrate 136 to the anatomical structure 146. Suitable fasteners include a snap, hook and loop, a magnetic latch, and/or other fasteners.

Figure 8:
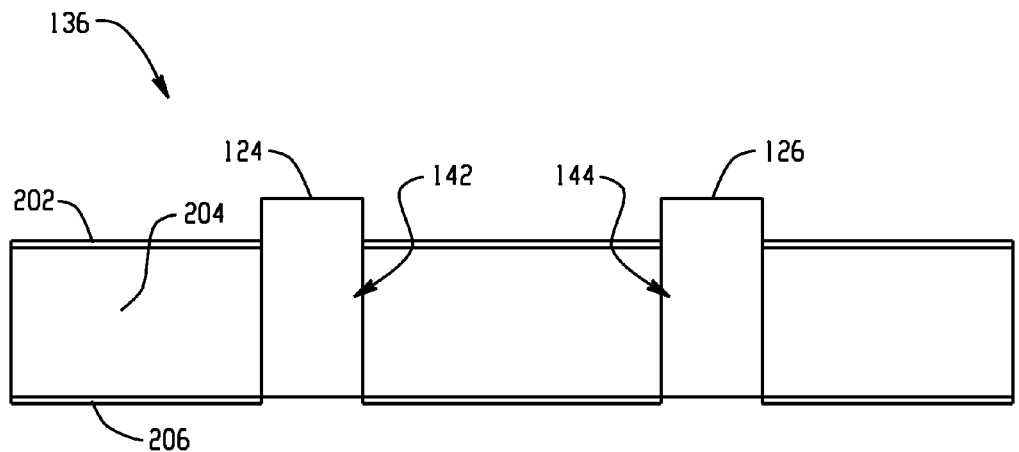
FIG. 8 illustrates an example substrate with channels extending the depth of the wells.

FIG. 8 illustrates an embodiment in which the channels 124 and 126 extend the entire or substantially the entire depth 208 of the wells 142 and 144. Such a configuration may facilitate increasing radiation emission and/or detection efficiency, or reducing radiation loss. Other depths of the channels 124 and 126 in the wells 142 and 144 are also contemplated herein.

Figure 9:
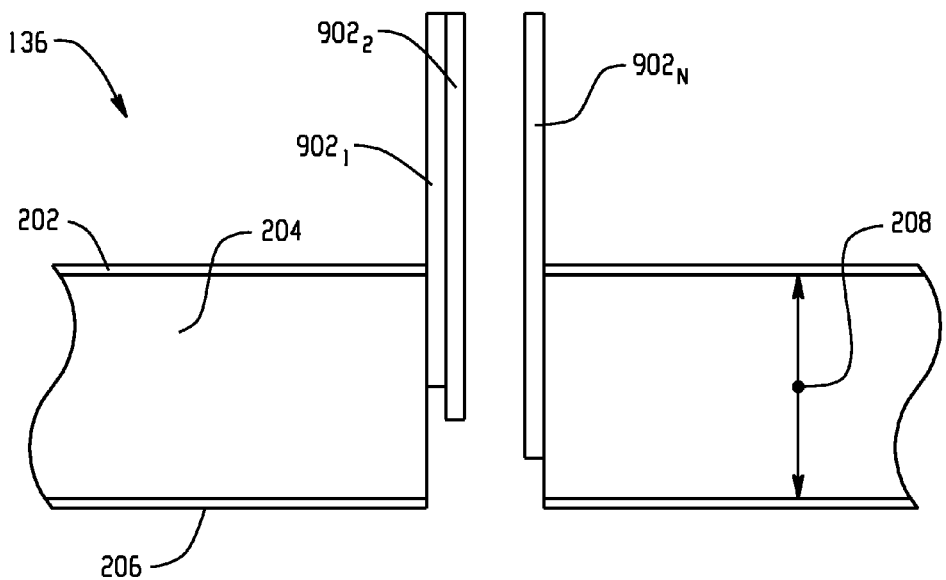
FIG. 9 illustrates an example substrate in which the individual fiber optic fibers of a channel extend different depths in the well.

FIG. 9 illustrates an embodiment in which individual fibers 902₁, 902₂, . . . , 902_N, of at least one of the channels (124 or 126) extend to different lengths along the depth 208. In another embodiment, the individual fibers 902₁, 902₂, . . . , 902_N may extend through separate wells in the substrate 136.

In another embodiment, the sheathing 148 is omitted.

In another embodiment, the optical couplers 128 and 132 are omitted.

Figure 10:
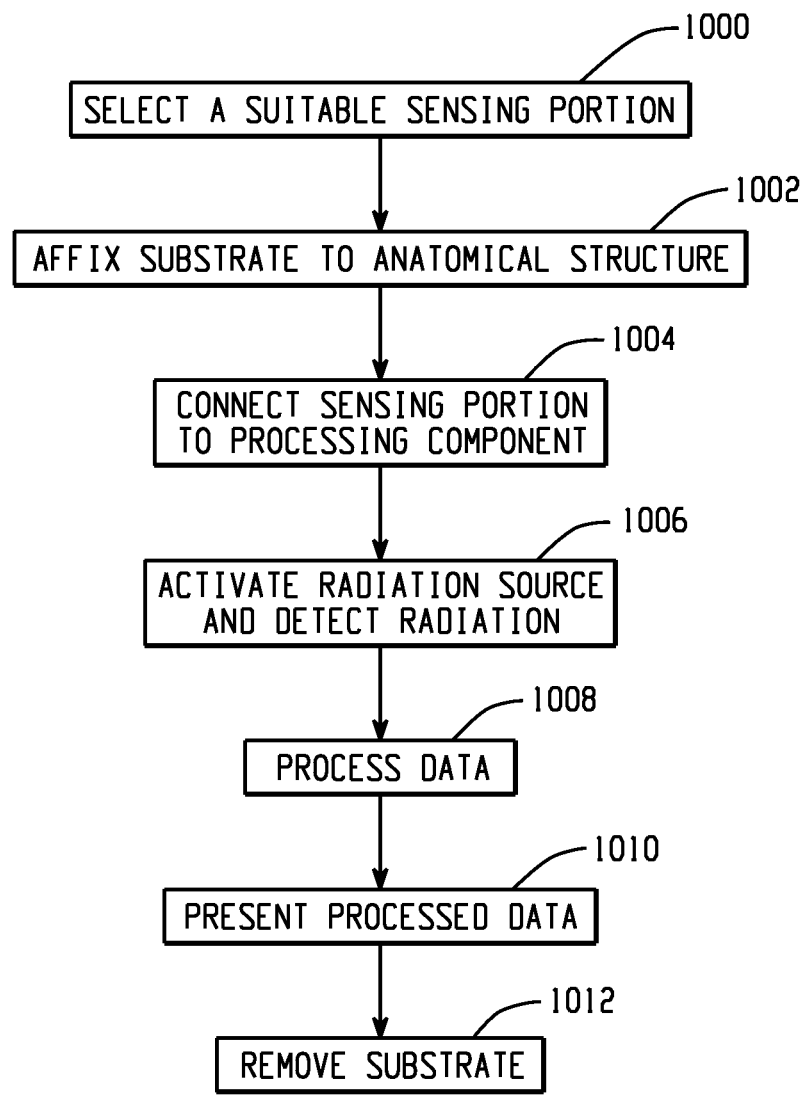
FIG. 10 illustrates a method for determining tissue oxygenation.

FIG. 10 illustrates a method for determining tissue oxygenation.

At 1000, a suitable sensing portion 122 is selected for the particular processing unit 102 being used.

At 1002, the substrate 136 of the selected sensing portion 122 is affixed to anatomical structure 146. As discussed herein, the substrate 136 carries the transmit and receive channels 124 and 126 and may include an adhesive surface 206 or a fastener 702, which facilitates affixing the substrate 136 to the anatomical structure 146.

At 1004, the other end of the sensing portion 122 is connected to the processing unit 102, if not already connected thereto.

At 1006, the source 116 is activated to emit radiation, which is routed, via the transmit channel 120, and illuminates the anatomical structure 146, and the detector 118 detects radiation traversing the anatomical structure 146 or reflected by the anatomical structure 146, depending on whether a transmission or a reflective based substrate 136 is employed.

At 1008, the detected signal is processed by the microprocessor 104 using instructions in the memory 106. In one instance, the microprocessor 104 executes instructions corresponding to an algorithm that determines tissue oxygenation information based on the detected signal.

At 1010, the processed data is presented on the display 110.

At 1012, the substrate 136 is removed from the anatomical structure 146.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A tissue oximeter sensor, comprising:
    a substrate with a non-zero finite depth and first and second major sides, wherein at least a first material free region extends along the depth from one of the sides to the other of the two sides forming a first well in the substrate, and one of the sides of the substrate is configured to be removeably affixed to a human or animal subject; and
    a first channel with first and second end portions, wherein one of the end portions of the first channel is selectively positioned in the first well along the depth alternatively at one of a plurality of different depth positions and the end portion does not extend beyond the first well on the side configured to be affixed to the subject, and the first channel routes radiation at least one of from the first end portion to the second end portion or from the second end portion to the first end portion.

2. The tissue oximeter sensor of claim 1, wherein the first channel includes a set of flexible fiber optic fibers.

3. The tissue oximeter sensor of claim 1, wherein the substrate is flexible and flexes to conform to a surface contour of the subject.

4. The tissue oximeter sensor of claim 1, wherein the selected depth determines at least one a radiation emission zone or a radiation detection zone.

5. The tissue oximeter sensor of claim 1, wherein the position of the first channel in the well corresponds to one or more of at least one of a predetermined emission electromagnetic radiation wavelength or a predetermined detection electromagnetic radiation wavelength, at least one of a predetermined electromagnetic radiation emission efficiency or a predetermined electromagnetic radiation detection efficiency, or a predetermined electromagnetic radiation source power consumption.

6. The tissue oximeter sensor of claim 1, wherein the end portion is an end of the first channel located between the two major sides of the substrate.

7. The tissue oximeter sensor of claim 1, further comprising:
    a radiation coupler coupled to the end portion that is not affixed in the well, wherein the coupler at least one of directs radiation to the first channel or directs radiation leaving the first channel.

8. The tissue oximeter sensor of claim 7, wherein the radiation coupler is an optical taper.

9. The tissue oximeter sensor of claim 1, further including an adhesive layer coupled to the side of the substrate configured to be removeably affixed to the human or animal subject.

10. The tissue oximeter sensor of claim 1, wherein at least a second material free region in the substrate extends along the depth from one of the sides to the other of the sides forming a second well in the substrate, and further comprising:
    a second channel with first and second end portions, wherein one of the end portions of the second channel is selectively positioned in the second well along the depth alternatively at one of a plurality of different depth positions and the end portion of the second channel does not extend beyond the second well on the side configured to be affixed to the subject,
    wherein the first channel routes radiation from the first end portion of the first channel to the second end portion of the first channel, and the second channel routes radiation from the second end portion of the second channel to the first end portion of the second channel.

11. The tissue oximeter sensor of claim 10, wherein the first and second wells are spaced apart from each other by a non-zero finite distance.

12. The tissue oximeter sensor of claim 11, wherein the distance corresponds to a predetermined spacing between a radiation emission zone of the first channel and a radiation detection zone of the second channel.

13. The tissue oximeter sensor of claim 10, wherein the first channel receives radiation from a radiation source located remote from the tissue oximeter sensor.

14. The tissue oximeter sensor of claim 10, wherein the second channel routes radiation to a detector located remote from the tissue oximeter sensor.

15. The tissue oximeter sensor of claim 10, further comprising a sheathing that surrounds the first and second channels.

16. The tissue oximeter sensor of claim 1, wherein the radiation has a wavelength in at least one of the visible or the near infrared regions of the electromagnetic spectrum.

17. The tissue oximeter sensor of claim 1, further comprising an interface configured to couple to a complementary interface of a tissue oximeter monitor.

18. A method, comprising: selectively installing a first end region of a set of flexible fiber optic fibers in a well of a tissue oximetry sensor substrate to one of a plurality of different depth positions in the well, wherein the installed position corresponds to a tissue oximetry processing algorithm of a given tissue oximetry processing unit and the end region does not extend beyond the well on the side of the substrate configured to be affixed to the subject.

19. The method of claim 18, further comprising:
coupling a second end region of the set of flexible fiber optic fibers to an optical coupler.

20. The method of claim 19, further comprising:
coupling the optical coupler to a communications interface configured to connect to a complementary communications interface of the tissue oximetry processing unit.

21. The method of claim 18, wherein the processing algorithm is based on one or more of an emission electromagnetic radiation wavelength, a detection electromagnetic radiation wavelength, an emission radiation efficiency, a detection radiation efficiency, or a radiation source power consumption.

22. The method of claim 18, wherein the substrate is configured to flex and flexes to conform to a surface contour of a subject to which the substrate is affixed.

23. The method of claim 18, further including selectively installing a second end region of a second set of flexible fiber optic fibers in a second well of the tissue oximetry sensor, wherein the sets of fiber are separated by a distance based on the tissue oximetry processing algorithm and the second end region does not extend beyond the second well on the side of the substrate configured to be affixed to the subject.

24. The method of claim 18, wherein the set of flexible fiber optic fibers receives radiation from a radiation source located remote from the substrate and routes the radiation to a destination.

25. The method of claim 18, wherein the set of flexible fiber optic fibers receives radiation and routes the radiation to a destination located remote from the substrate.

26. A physiological parameter monitoring apparatus, comprising:
a processing unit, including an optical source and an optical detector;
flexible optical transmit and receive channels having first and second end regions; and
a flexible substrate that carries the first end regions of the flexible optical transmit and receive channels, wherein the first end regions are installed at predetermined depths of the flexible substrate, the installed depths correspond to a tissue oximetry processing algorithm of the processing unit, the flexible optical transmit channel routes optical radiation emitted by a source from the second end region of the flexible optical transmit channel to a target adjacent the first end region, and the flexible optical receive channel routes optical radiation traversing or reflecting from the target to the detector, wherein the first end region does not extend beyond the substrate on a side configured to be affixed to the subject.

* * * * *